US00PP25383P2

(12) United States Plant Patent
Verduin

(10) Patent No.: US PP25,383 P2
(45) Date of Patent: Mar. 24, 2015

(54) ***ASTILBE* PLANT NAMED 'NEW WAVE'**

(50) Latin Name: ***Astilbe* hybrid**
Varietal Denomination: New Wave

(71) Applicant: Henricus Gijsbertus Johannes Verduin, Heemskerk (NL)

(72) Inventor: Henricus Gijsbertus Johannes Verduin, Heemskerk (NL)

( * ) Notice: Subject to any disclaimer, the term of this patent is extended or adjusted under 35 U.S.C. 154(b) by 88 days.

(21) Appl. No.: 13/815,447

(22) Filed: Mar. 4, 2013

(51) Int. Cl.
*A01H 5/00* (2006.01)

(52) U.S. Cl.
USPC ..... Plt./407

(58) Field of Classification Search
USPC ..... Plt./407
See application file for complete search history.

(56) References Cited

PUBLICATIONS

PLUTO Plant Variety Database 2014-04 search for New Wave plant p. 1.*

* cited by examiner

*Primary Examiner* — Annette Para
(74) *Attorney, Agent, or Firm* — Penny J. Aguirre

(57) ABSTRACT

A new cultivar of *Astilbe* named 'New Wave' that is characterized by its uniformly colored light pink flowers that are consistent in color throughout the inflorescence and between inflorescences, its upright flower spikes, and its effective and fast propagation by division.

2 Drawing Sheets

Botanical classification: *Astilbe* hybrid.
Varietal denomination: 'New Wave'.

BACKGROUND OF THE INVENTION

The present invention relates to a new and distinct cultivar of *Astilbe* of hybrid origin and will be referred to hereafter by its cultivar name, 'New Wave'. 'New Wave' represents a new *Astilbe*, an herbaceous perennial grown for landscape use.

The new cultivar of *Astilbe* arose from a breeding program conducted by the Inventor in Heemskerk, The Netherlands with the goal of developing an Astile cultivar with uniformly colored light pink flowers. 'New Wave' originated as a seedling that arose from seed planted from open pollination of 'Europa' (not patented) in 2004. 'New Wave' was selected as a single unique plant in July of 2006 from amongst the resulting seedlings.

Asexual propagation of the new cultivar was first accomplished by division by the Inventor in Heemskerk, The Netherlands in January of 2007. Asexual propagation by division has determined that the characteristics of the new cultivar are stable and are reproduced true to type in successive generations.

SUMMARY OF THE INVENTION

The following traits have been repeatedly observed and represent the characteristics of the new cultivar as observed in Heemskerk, The Netherlands. These characteristics in combination distinguish 'New Wave' as a unique cultivar of *Astilbe*.

1. 'New Wave' exhibits uniformly colored light pink flowers that are consistent in color throughout the inflorescence and between inflorescences.
2. 'New Wave' exhibits effective and fast propagation.
3. 'New Wave' exhibits upright flower spikes.

The female parent of 'New Wave', 'Europa', differs from 'New Wave' in having inflorescences that are less dense with flowers that vary from white to clear pink in color, and in having less effective propagation (less plants can be produced through division per plant). 'New Wave' can be most closely compared to the cultivars: 'Peach Blossom' (not patented) and 'Elizabeth Bloom' (not patented). 'Peach Blossom' differs from 'New Wave' in producing less inflorescences with flowers that are not as uniform in color. 'Elizabeth Bloom' differs from 'New Wave' in having inflorescences that vary in color from very light pink to medium pink.

BRIEF DESCRIPTION OF THE PHOTOGRAPHS

The plants in the photographs depict a 14 month-old plant of 'New Wave' as grown in a greenhouse in a 3-liter container in Heemskerk, The Netherlands.

Figure 1:
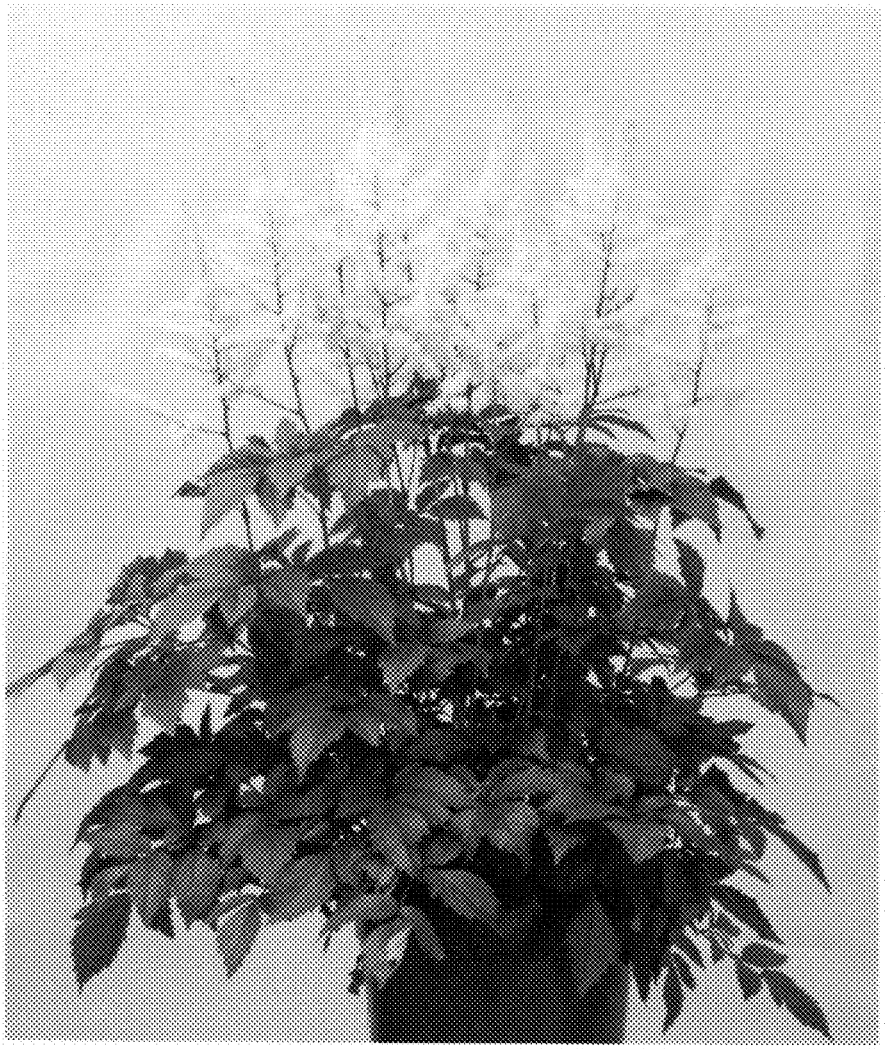

The photograph in FIG. 1 provides a side view of the new 'New Wave' in bloom.

Figure 2:
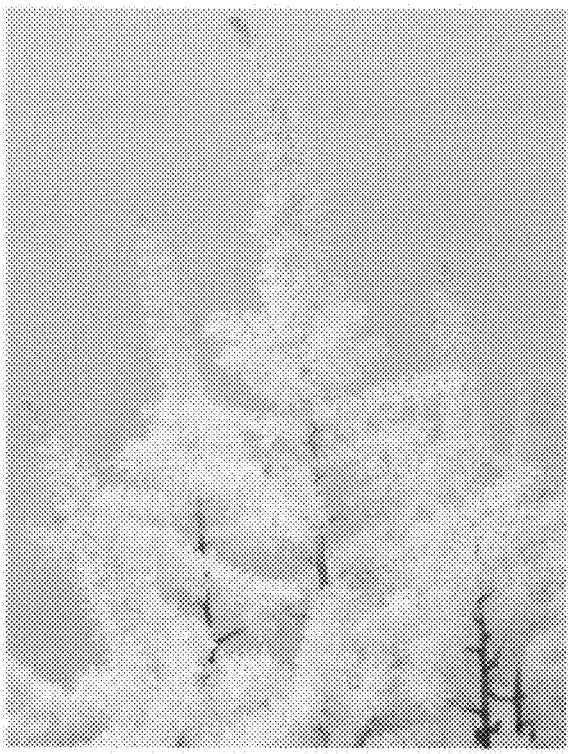

The photograph in FIG. 2 provides a close-up view of an inflorescence of 'New Wave'.

Figure 3:
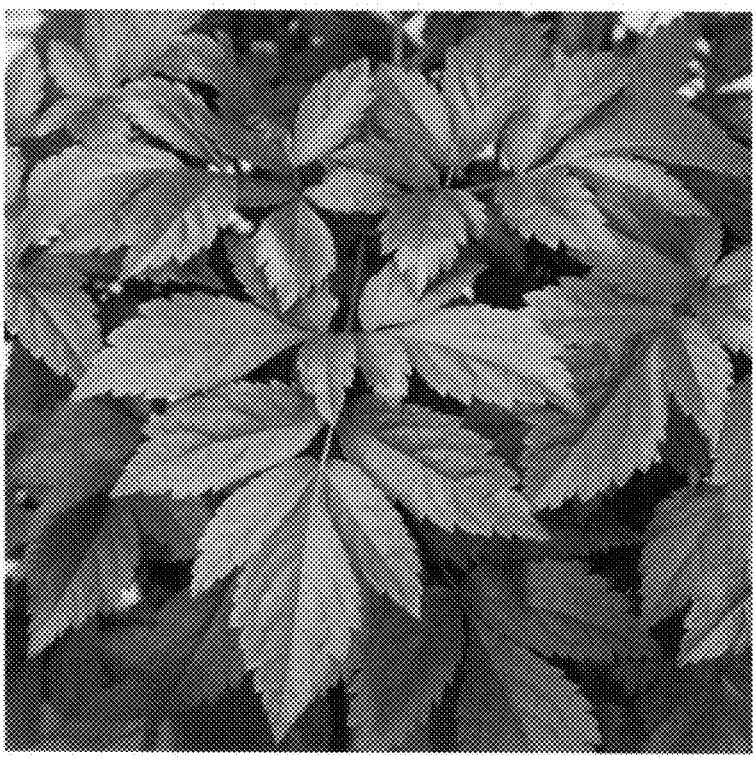

The photograph in FIG. 3 provides a close-up the foliage of 'New Wave'.

The colors in the photographs are as close as possible with the digital photography and printing techniques utilized and the color codes in the detailed botanical description accurately describe the colors of the new *Astilbe*.

DETAILED BOTANICAL DESCRIPTION

The following is a detailed description of 14-month-old plants as grown in a greenhouse in 3-liter containers in Heemskerk, The Netherlands. Plants were grown under average day temperatures ranging from 15° to 20° C. and average night temperatures ranging from 12° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late June into July in The Netherlands.

*Plant type.*—Herbaceous perennial.

*Plant habit.*—Clump-forming, broadly upright with upright blooming stems.

*Height and spread.*—50 to 60 cm in height and spread when mature in the landscape.

*Hardiness.*—At least to U.S.D.A. Zone 5.

*Diseases and pests.*—Has been observed to have healthy foliage, no particular disease or pest resisitance or susceptibility has been observed.

*Propagation.*—Division (during winter dormancy).

*Growth rate.*—Moderate to moderately high, quick and effective to propagate.

Stem description (flowering stems):

*Stem color.*—143A and 144A.

*Stem shape.*—Round.

*Stem size.*—Average of 29.4 cm in length and 3 mm in diameter.

*Stem quantity.*—Average of 11 main stems.

*Stem surface.*—Moderately glossy.

*Stem aspect.*—Very strong, mostly held upright.

*Branching habit.*—No lateral branches, stems grow from the base.

Foliage description:

*Leaf division.*—Compound.

*Leaf attachment.*—Petiolate.

*Leaf arrangement.*—Alternate.

*Leaf shape.*—Biternate, broad ovate in outline.

*Leaf number.*—Average of 3 per lateral branch.

*Internode length.*—Average of 11.5 cm.

*Leaf size.*—Average of 17.1 cm in length (excluding petiole) and 18.2 cm in width.

*Leaf color.*—Young foliage upper surface; between 137B and 143A, young foliage lower surface; 137B to 137C, mature foliage upper surface; N137A, mature foliage lower surface; 138A.

*Leaflet quantity.*—Average of 27 per leaf.

*Leaflet shape.*—Elliptic.

*Leaflet base.*—Acuminate.

*Leaflet apex.*—Apiculate.

*Leaflet venation.*—Pinnate, color of upper surface; 146B, color of lower surface; 138B.

*Leaflet margins.*—Biserrate.

*Leaflet size.*—Average of 5.3 cm in length and 2.5 cm in width.

*Leaflet and leaflet surface.*—Both surfaces moderately glossy, slightly rough to the touch due to being sparsely covered with short strigose hairs, average length 0.5 mm, 157D in color.

*Petioles.*—Leaf; average of 10.2 cm in length, 2 mm in diameter and 143B to 143C in color, glabrous surface, petiolules of leaflet; average of 9 mm in length and 1 mm in diameter, 143B to 143C in color, glabrous surface.

*Stipules.*—Both sides of the leaf base have a dry leafy stipule, ovate in shape, average of 5 mm in length, 2.5 mm in width and N199C to N199D in color.

Flower description:

*Inflorescence type.*—Numerous single rotate shaped flowers arranged on pyramidal panicles.

*Inflorescence aspect.*—Upright and held above foliage.

*Inflorescence size.*—Average of 19.3 cm in height and 14.5 cm in width.

*Flower fragrance.*—Strong, sweet and pleasant fragrance.

*Flower quantity.*—Average of 800 per inflorescence.

*Flower lastingness.*—Average of 10 days.

*Flower buds.*—Broadly elliptic in shape, average of 2 mm in length and 1.25 mm in diameter, color; 65A, base 145C to 145D.

*Flower aspect.*—Upright, outward, and drooping.

*Flower shape.*—Rotate.

*Flower size.*—About 4 mm in depth and 6 mm in diameter.

*Petals.*—Average of 5, oblanceolate in shape, margin is entire, apex is broadly acute, average of 4 mm in length and 1 mm in width, color: upper and lower surface when opening; between 65B and 68D, upper and lower surface when fully open; 69C to 69D, both surfaces fading to 69D and finally N155B as they age.

*Calyx.*—Campanulate, average of 1.5 mm in length and 2.5 mm in diameter.

*Sepals.*—5, ovate in shape, margin is entire, apex is acute, base is cuneate and fused, surface is smooth and dull, color of upper and lower surface when immature; 145C to 145D, color of upper and lower surface when mature; 150D, about 0.75 mm in width and 1.5 mm in length.

*Peduncles.*—Average of 18.9 cm in length and 1.5 mm in diameter, held at 0° (straight upright), peduncles of secondary racemes; held at an average angle of 40°, strong, color is 145B, glabrous surface.

*Pedicels.*—About 1.5 mm in length and 0.5 mm in width, held at an average angle of 45°, 150D in color, glabrous surface.

Reproductive organs:

*Gynoecium.*—2 Pistils, about 1 mm in length, stigma is club-shaped and 155A in color, style is about 0.8 mm in length and 155A in color, ovary is 155A in color.

*Androcoecium.*—About 10 stamens, anthers are ovate in shape, basifixed, about 0.2 mm in length and 85A to 85B in color, filaments are about 2 mm in length and 65D in color, pollen is very low in quantity and N155A in color.

*Seed and fruit.*—No seeds or fruit have been detected to date.

It is claimed:

1. A new and distinct cultivar of *Astilbe* plant named 'New Wave' as herein illustrated and described.

* * * * *